United States Patent
Düppenbecker et al.

(10) Patent No.: US 12,429,542 B2
(45) Date of Patent: Sep. 30, 2025

(54) APPARATUS AND METHOD FOR INTERFERENCE SUPPRESSION IN A MAGNETIC RESONANCE TOMOGRAPHY UNIT

(71) Applicant: Siemens Healthcare GmbH, Erlangen (DE)

(72) Inventors: Peter Michael Düppenbecker, Herzogenaurach (DE); Andrei-Vasile Tunea, Erlangen (DE); Andreas Fackelmeier, Thalmässing (DE)

(73) Assignee: Siemens Healthineers AG, Forchheim (DE)

(*) Notice: Subject to any disclaimer, the term of this patent is extended or adjusted under 35 U.S.C. 154(b) by 51 days.

(21) Appl. No.: 18/231,911

(22) Filed: Aug. 9, 2023

(65) Prior Publication Data

US 2024/0069133 A1    Feb. 29, 2024

(30) Foreign Application Priority Data

Aug. 25, 2022    (EP) .................................. 22192157

(51) Int. Cl.
| | |
|---|---|
| *G01R 33/48* | (2006.01) |
| *A61B 5/055* | (2006.01) |
| *G01R 33/36* | (2006.01) |
| *G01R 33/422* | (2006.01) |
| *G01R 33/56* | (2006.01) |

(52) U.S. Cl.
CPC ..... *G01R 33/4808* (2013.01); *G01R 33/3692* (2013.01); *G01R 33/422* (2013.01); *G01R 33/5608* (2013.01); *A61B 5/055* (2013.01)

(58) Field of Classification Search
CPC ............ G01R 33/3692; G01R 33/5608; G01R 33/422; G01R 33/4808
See application file for complete search history.

(56) References Cited

U.S. PATENT DOCUMENTS

| | | | |
|---|---|---|---|
| 6,469,515 B2* | 10/2002 | Borsi | G01R 33/385 324/536 |
| 11,199,598 B2 | 12/2021 | Biber et al. | |
| 2014/0253125 A1* | 9/2014 | Sakakura | G01R 33/3856 324/322 |
| 2017/0108569 A1* | 4/2017 | Harvey | G01R 33/36 |
| 2017/0307701 A1 | 10/2017 | Leussler et al. | |
| 2019/0086497 A1 | 3/2019 | Rearick et al. | |
| 2021/0103018 A1 | 4/2021 | Biber et al. | |
| 2021/0302523 A1 | 9/2021 | Grodzki et al. | |

FOREIGN PATENT DOCUMENTS

| | | |
|---|---|---|
| DE | 102020204167 A1 | 9/2021 |
| EP | 3800479 A1 | 4/2021 |
| WO | 2019068687 A2 | 4/2019 |

* cited by examiner

*Primary Examiner* — Gregory H Curran
(74) *Attorney, Agent, or Firm* — Lempia Summerfield Katz LLC

(57) ABSTRACT

The disclosure relates to an electronic apparatus for a magnetic resonance tomography unit, a system including an electronic apparatus, a magnetic resonance tomography unit, and a method for operation. The apparatus has a detector for detecting a source of interference. The detected signal interferes with image acquisition.

18 Claims, 4 Drawing Sheets

APPARATUS AND METHOD FOR INTERFERENCE SUPPRESSION IN A MAGNETIC RESONANCE TOMOGRAPHY UNIT

The present patent document claims the benefit of European Patent Application No. 22192157.0, filed Aug. 25, 2022, which is hereby incorporated by reference in its entirety.

TECHNICAL FIELD

The disclosure relates to an electronic apparatus for a magnetic resonance tomography unit and a magnetic resonance tomography unit and a method for operation. The apparatus has a sensor for detecting electromagnetic interference fields. The detected signal interferes with image acquisition.

BACKGROUND

Magnetic resonance tomography units are imaging apparatuses that align nuclear spins of the object under examination with a strong external magnetic field for imaging of an object under examination and, by an alternating magnetic field, excite them to precession around this alignment. The precession or return of the spins from this excited state to a state with lower energy in turn generates a magnetic alternating field in response, which is received via antennae.

With the aid of magnetic gradient fields, spatial encoding is impressed on the signals, which subsequently enables an assignment of the received signal to a volume element. The received signal is then evaluated and a three-dimensional imaging representation of the object under examination is provided. To receive the signal, local receiving antennae, so-called local coils, may be used. The receiving antennae may be arranged directly on the object under examination in order to achieve a better signal-to-noise ratio. The receiving antennae may also be installed in a patient couch.

Magnetic resonance tomography units require high-frequency shielding in two respects. For one thing, high-frequency pulses with a power output in the kilowatt range, which are only partially absorbed in the patient, are generated to excite the nuclear spins. Radio waves that leave the patient feedthrough are emitted into the room and are therefore screened for compliance with emission limit values.

Conversely, the magnetic resonance signals to be received for imaging are extremely weak. In order to achieve a sufficient signal-to-noise ratio (SNR) here, a shielding of external interference signals is required.

Therefore, in the prior art, complex shielding cabins are installed around a magnetic resonance tomography unit in order to reduce both emissions as well as immissions.

A method and an apparatus for interference suppression in magnetic resonance imaging is known from the application WO 2019/068687.

SUMMARY AND DESCRIPTION

It is therefore an object of the disclosure to improve the imaging in an environment with interfering high-frequency signals.

This object is achieved by an apparatus, a system, and a method as disclosed herein. The scope of the present disclosure is defined solely by the appended claims and is not affected to any degree by the statements within this summary. The present embodiments may obviate one or more of the drawbacks or limitations in the related art.

The electronic apparatus is configured for use jointly or as part of a magnetic resonance tomography unit. This is to be understood in particular as meaning that the electronic apparatus is in operation while image acquisition is carried out with the magnetic resonance tomography unit. The electronic apparatus may be a local coil connected wirelessly or via cables, or a medical device or sensor for monitoring or communicating with the patient, a display, terminal, or other control element for monitoring or controlling image acquisition. The electronic apparatus may have components that generate electromagnetic alternating fields during operation and may thus cause interference with image acquisition. These components may be processors, digital circuits, oscillators, or inverters. Electronic or mechanical switches also generate pulse-like interference fields.

The apparatus has a detector for detecting a source of interference. The detector may directly detect electrical and/or magnetic interference fields of the source of interference, as explained below. It is also conceivable, however, for the source of interference to be detected indirectly. For example, the activity of a circuit may be monitored via the power supply and thus interference caused by these activities may be inferred. The detector may also include logic or software that monitors the activities currently being carried out in the apparatus, either by itself having started these activities or by accessing a controller of the electronic apparatus. The information then has an identification for the activity.

Furthermore, the electronic apparatus has a signal output. The signal output may be an electrical cable and/or plug-in connection. An optical cable connection is also conceivable. However, wireless transmission through the free space between the electronic apparatus and the magnetic resonance tomography unit would also be possible, for example, by analog or digital radio transmission or optical transmission in the visible or infrared wavelength range. Radio transmission may also be considered to be frequencies above a Larmor frequency of the magnetic resonance tomography unit, for example, in the GHz range, e.g., in ISM bands with lower regulatory restrictions. Electrical high-frequency transmission by inductive or capacitive coupling would also be conceivable. The signal may be transmitted to the magnetic resonance tomography unit via the signal output as a function of the electromagnetic interference fields.

The system has an electronic apparatus as disclosed herein and a magnetic resonance tomography unit. The electronic apparatus may be part of the image acquisition by the magnetic resonance tomography unit or supports this, for example, by additional data or during operation.

The magnetic resonance tomography unit of the system has a signal input. The signal input is configured to be complementary to the signal output of the electronic apparatus, so that the magnetic resonance tomography unit may be brought into signal connection with the sensor via the signal output of the electronic apparatus and the signal input of the magnetic resonance tomography unit in order to receive the information about the source of interference from the detector of the electronic apparatus. The magnetic resonance tomography unit is configured to perform image acquisition as a function of the information of the detector. For example, the information may be used to interrupt and/or repeat detection in the event of signaling of interference by the detector. It is also conceivable to activate a filter in accordance with the information. If the information is a detected interference signal, then for the sake of reduction the detected interference signal with adjusted amplitude and phase position may be mixed with a detected magnetic resonance signal for destructive interference.

Finally, the information may be stored in order to be able to recognize and/or suppress artifacts subsequently during the image reconstruction itself. For example, a correlation between the magnetic resonance signal and the stored reference signal may be determined with a reference signal stored for the activity of the source of interference and information about the time of activity and said reference signal may then be removed from the magnetic resonance data or suppressed in the image reconstruction.

Advantageously, the system includes the electronic apparatus in conjunction with a magnetic resonance tomography unit correspondingly configured for interaction with the electronic apparatus enables particularly effective and reliable suppression of interference by the electrical apparatus.

The method is provided for operation of a system as disclosed herein in order to generate a magnetic resonance image.

In one act of the method, a high-frequency excitation pulse is emitted by the magnetic resonance tomography unit via an antenna such as, for example, a body coil or local coil into an object under examination or a patient in order to generate an alternating high-frequency magnetic field therein, to excite the nuclear spins of the object under examination with the magnetic resonance tomography unit in a static or quasi-static magnetic field of a field coil and/or gradient coil for precession.

In a further act of the method, the magnetic resonance tomography unit receives a magnetic resonance signal of the object under examination for image acquisition via a receiving antenna, for example, the body coil or a local coil.

In another act, the magnetic resonance tomography unit receives information about the source of interference via the signal input. This may be information about an activity of the source of interference that causes interference or directly a signal to an electromagnetic interference field. Receiving the signal to the detected interference field may include receiving an analog signal of the sensor and its further processing, but may also be a signal preprocessed and/or digitized, for example, in the electronic apparatus. Receiving may also include storing the information in a memory of the magnetic resonance tomography unit, in particular, with a time reference to the received magnetic resonance signal.

In a further act, the magnetic resonance tomography unit reduces an effect of the electromagnetic interference field during image acquisition as a function of the signal. Various possibilities have already been described above in connection with the system.

The method shares the advantages of the system.

In a conceivable embodiment of the electronic apparatus, the detector is a sensor for detecting electromagnetic interference fields, such as may be caused, for example, by the components of the electronic apparatus described above. The sensor may be an electrical or magnetic antenna. It is also conceivable for the sensor to detect the electromagnetic interference fields indirectly, for example, by detecting voltages or currents in conductors in an ohmic, capacitive, or inductive manner. The sensor may generate a signal that is dependent on or proportional to a field strength of the electrical and/or magnetic component of the interference field or its envelope curve.

Advantageously, the electronic apparatus makes it possible to detect electromagnetic interference fields directly at the source in the electromagnetic apparatus by the sensor, and thus to facilitate the subsequent suppression thereof by an interference signal that is as unchanged as possible.

In an embodiment of the electronic apparatus, the sensor is arranged in the immediate vicinity of a source of an electromagnetic interference field. The source of interference may be part of the electronic apparatus, (e.g., part of analog or digital processing, and/or transmission technology for the magnetic resonance signal). In particular, complex digital signal processing modules have a barely predictable spectrum of emitted frequencies that may also change with the processed signals in an unpredictable manner. If the sensor is arranged in the immediate vicinity of a source of interference, the sensor may absorb the signals of the source of interference based on the distance dependence of the electrical and/or magnetic fields. The sensor may also be electrically connected, for example, to connecting lines of the source, such as the interfering electronic component, in order to detect an interference signal in this manner.

In an advantageous manner, a signal of the sensor, which represents the interference signal in a particularly pure form, enables particularly effective interference suppression of the image acquisition.

In one possible embodiment of the electronic apparatus, the electronic apparatus has a shield. An arrangement that attenuates electrical and or magnetic fields, in particular high-frequency alternating fields, on the way into an interior of the electronic apparatus or, because of the reversibility, also during propagation from the source in the electronic apparatus in the direction of propagation, is regarded as a shield. The shield may include an electrically conductive material. In this case, the electrically conductive material encloses the source and the sensor completely or entirely. For example, as a housing of the electronic apparatus or as a separate apparatus inside or outside the housing, the shield may jointly enclose the sensor and the source in a cavity surrounded by the shield. It is also conceivable for the shield to have one or more openings for feedthroughs. Partial shielding, which surrounds the sensor and source in only one or several of six possible spatial directions, is also possible. In order to avoid eddy currents, it is also conceivable for the shield to have slots or holes. The shield may be made of a material that conducts electricity well, such as a metal. The shield may not be ferromagnetic in this case. The object under examination or patient may not be inside the shield, not even with individual body parts.

A conductive plastic such as carbon fiber-containing material, is also possible. The comparatively lower conductivity reduces problems caused by eddy currents.

By virtue of the fact that the sensor and the source are at least partially surrounded by a shield, magnetic resonance signals of the object under examination are attenuated on the way to the sensor, so that the sensor supplies a signal that is virtually free or independent of components of the magnetic resonance signal, wherein a magnetic resonance signal at this point is not intended to mean signals derived from the magnetic resonance signal such as in the case of a local coil in the apparatus, but rather the currents and voltages directly induced by the alternating fields of the nuclear spins. This almost pure interference signal of the sensor advantageously reduces artifacts that are caused in the subsequent interference suppression in signal processing or image reconstruction by magnetic resonance signal components that are erroneously interpreted and processed as interference signals.

In one possible embodiment of the method, reference data relating to a source of interference is acquired in one act. This reference data relates in particular to the emission of electrical and/or magnetic interference fields during a predetermined activity of the source of interference. In one case, the reference data may be samples of digitized interference signals during the activity. For example, data derived therefrom, such as averaged values or spectral information, is also possible.

In the act of reducing an effect of the source of interference, the effects of the activity are then reduced as a function of the reference data.

It is conceivable, for example, that the reference data is a sample of an emission of the source of interference during the predetermined activity. The emission may be identical during each execution of the activity by the source of interference. Then, for example, by an autocorrelation, (e.g., using a time stamp from the information about the activity), a portion of the interference signal caused by the activity may be detected in the magnetic resonance data and reduced, for example, by subtraction. If the data is not identical, filtering and a reduction may nevertheless take place, for example, using specific spectral information. Methods of machine learning and artificial intelligence or correspondingly trained neural networks may also anticipate the transformation of a measured interference signal and the resulting interference in the magnetic resonance signal and reduce or eliminate the interference in the generated image.

The properties, features, and advantages of the disclosure described above and the manner in which these are achieved become clearer and more comprehensible in connection with the following description of the exemplary embodiments, which are described in more detail in connection with the drawings.

DETAILED DESCRIPTION

Figure 1:
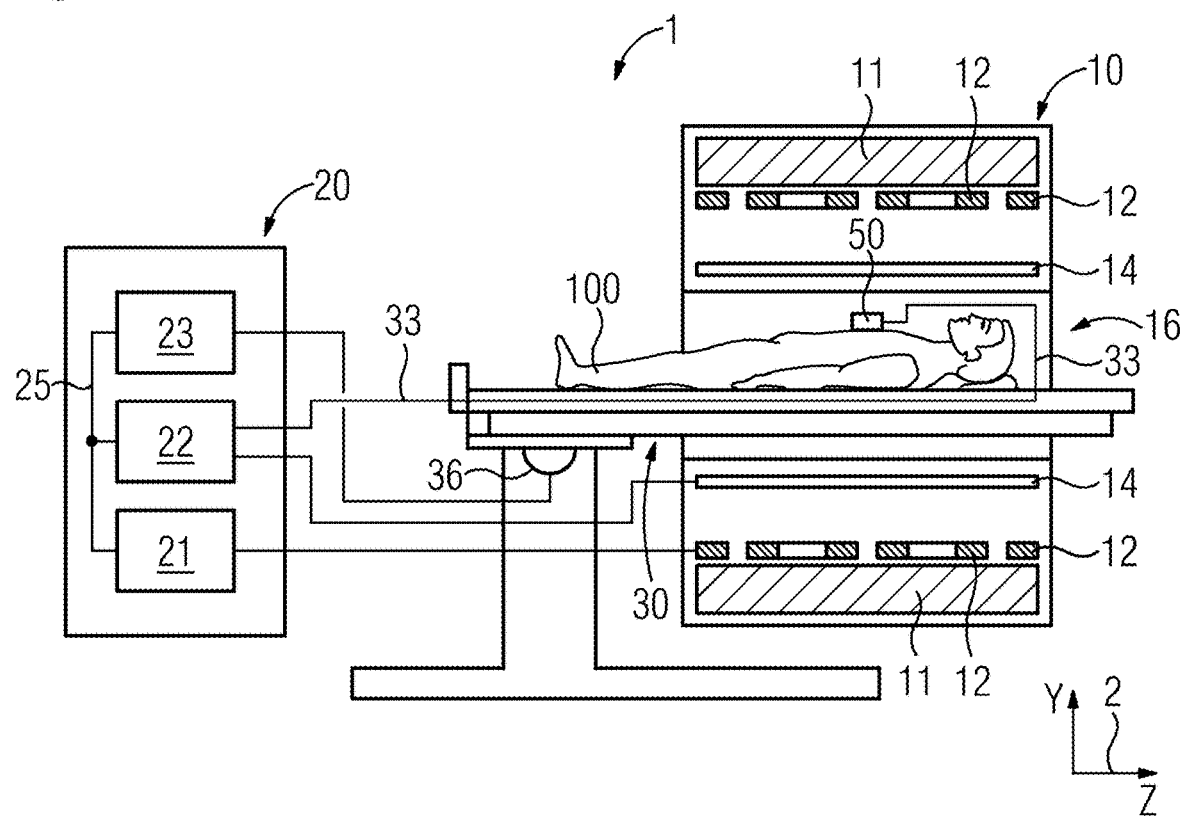
FIG. 1 depicts a diagrammatic view of an example of a magnetic resonance tomography unit with an electronic apparatus.

FIG. 1 shows a diagrammatic view of an embodiment of a magnetic resonance tomography unit 1 with an electronic apparatus, here a local coil 50.

The magnetic unit 10 has a field magnet 11 that generates a static magnetic field B0 for aligning nuclear spins of samples or of the patient 100 in a receiving region. The receiving region is characterized by an extremely homogeneous static magnetic field B0, wherein the homogeneity relates in particular to the magnetic field strength or the magnitude. The receiving region is almost spherical and is arranged in a patient tunnel 16 that extends in a longitudinal direction 2 through the magnetic unit 10. A patient couch 30 may be moved in the patient tunnel 16 by the traversing unit 36. The field magnet 11 may be a superconducting magnet that may provide magnetic fields with a magnetic flux density of up to 3T, or even higher in the latest devices. However, permanent magnets or electromagnets with normally conducting coils may also be used for lower magnetic field strengths.

Furthermore, the magnetic unit 10 has gradient coils 12 configured to superimpose temporally and spatially variable magnetic fields in three spatial directions on the magnetic field B0 in order to spatially differentiate the acquired imaging regions in the examination volume. The gradient coils 12 may be coils of conducting wires that may generate orthogonal fields in the examination volume with respect to one another.

The magnetic unit 10 likewise has a body coil 14 configured to emit a high-frequency signal supplied via a signal line into the examination volume and to receive resonance signals emitted by the patient 100 and to emit them via a signal line.

A control unit 20 supplies the magnetic unit 10 with the various signals for the gradient coils 12 and the body coil 14 and evaluates the received signals.

Thus, the control unit 20 has a gradient controller 21 configured to supply the gradient coils 12 via supply lines with variable currents, which provide the desired gradient fields in the examination volume in a temporally coordinated manner.

Furthermore, the control unit 20 has a high-frequency unit 22 configured to generate a high-frequency pulse with a predetermined time profile, amplitude, and spectral power distribution for exciting a magnetic resonance of the nuclear spins in the patient 100. Pulse power in the range of kilowatts may be achieved. The excitation signals may be emitted into the patient 100 via the body coil 14 or also via a local transmitting antenna.

A controller 23 communicates with the gradient controller 21 and the high-frequency unit 22 via a signal bus 25.

To receive the magnetic resonance signal, a local coil 50 is arranged on the patient 100 in the patient tunnel 16 in order to detect magnetic resonance signals from an examination region in the immediate vicinity with the greatest possible signal-to-noise ratio. The local coil 50 is in signal connection with a receiver in the high-frequency unit 22 via a connecting line 33.

In this case, the local coil 50 is an electronic apparatus that, as shown in detail in the following figures, has a source of interference and a sensor 70. In this case, the sensor 70 is configured to detect electromagnetic interference fields generated by the source of interference and to transmit information about the electromagnetic interference fields generated by the source of interference via the connecting line 33 as a signal connection, which information is suitable for reducing or preventing a disadvantageous effect on the subsequent signal processing and/or image reconstruction.

Figure 2:
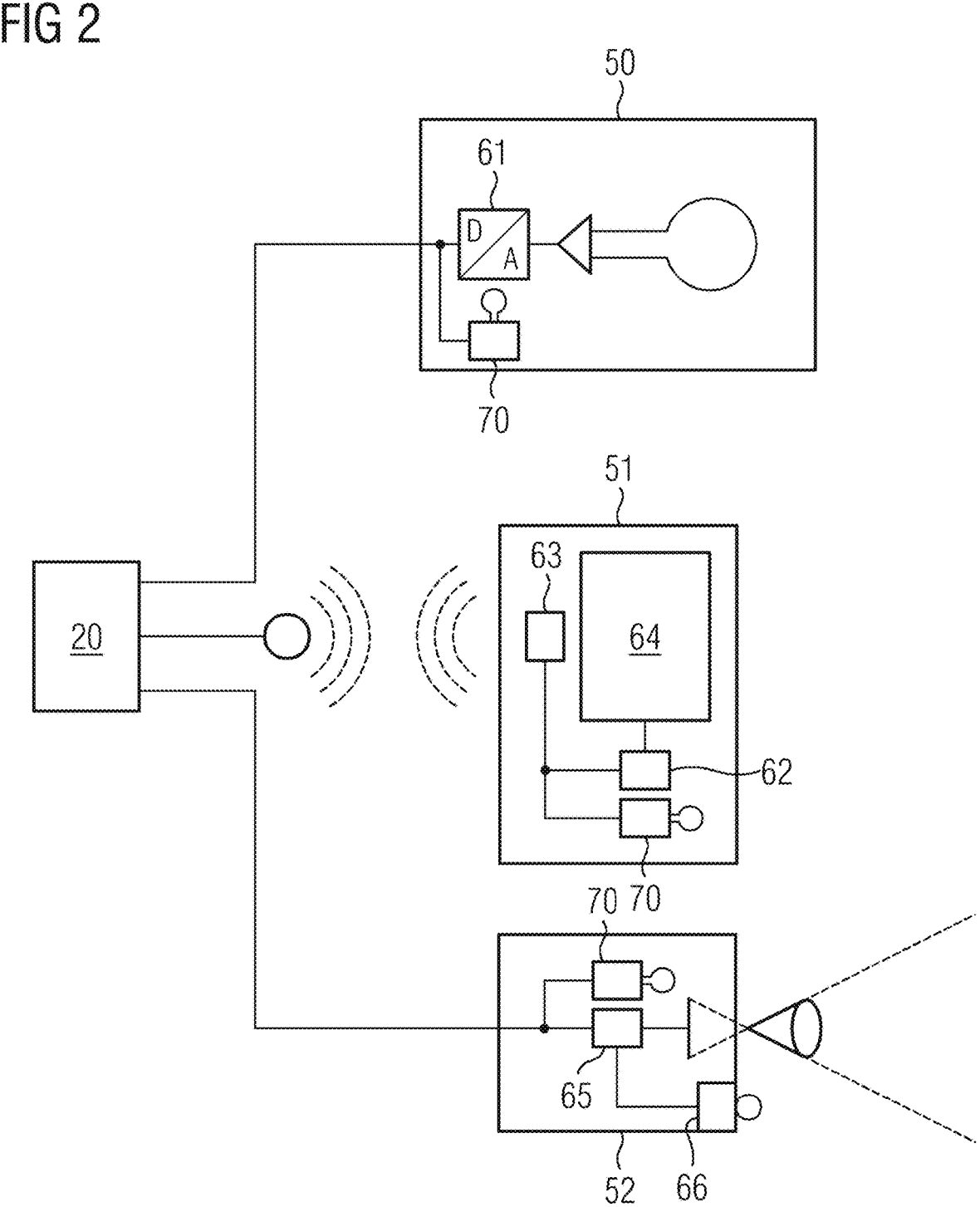
FIG. 2 depicts a diagrammatic view of examples of different electronic apparatuses.

FIG. 2 shows a diagrammatic view of different electronic apparatuses. By way of example, a local coil 50, a tablet computer 51 for operation and a monitoring camera 52 for monitoring of and communication with the patient 100 during image acquisition are specified here for electronic apparatuses.

The local coil 50 may have an analog-to-digital converter 61 as a source of interference that digitizes a received magnetic resonance signal before transmission to the magnetic resonance tomography unit 1 or to the high-frequency unit 22 of the control unit 20. A sensor 70 is arranged in the local coil 50 in the vicinity of the A/D converter 61 in order to detect the interference fields generated by the A/D converter 61 in as undistorted a manner as possible and with a large signal-to-noise ratio. The sensor 70 may analogously transmit the detected interference signals in a shielded connecting line to the high-frequency unit 21. Digitization and multiplexing with the digitized magnetic resonance data is also conceivable. In order to prevent artifacts due to magnetic resonance signals detected by the sensor 70, it is also possible to detect the signals of the sensor 70 in phases without magnetic resonance signals in order to obtain interference signals without magnetic resonance signal components and thus to distinguish these from magnetic resonance signals or to learn their characteristics.

By way of example, a tablet computer 51 is shown here as an electronic apparatus with wireless connection via a radio unit 63. The radio unit 63 may use the digital standards Bluetooth or WLAN, but other approved radio services are also conceivable that provide the required bandwidth, provide sufficient transmission security with regard to data loss and comply with the legal regulations. Most of these radio services are based on digital transmission, wherein, in addition to the wave ranges used for transmission, interference signals are also produced by the digital processing on other interfering frequency ranges such as the Larmor frequency of the magnetic resonance tomography unit 1. Similarly, a processor 62 or a display 64 generates interference fields. Here, too, the sensor 70 detects these interference fields directly at the point of origin and transmits information for interference suppression to the control unit 20, here on the wireless path via the radio unit 63. The same applies to a local coil 50 with wireless transmission.

Figure 3:
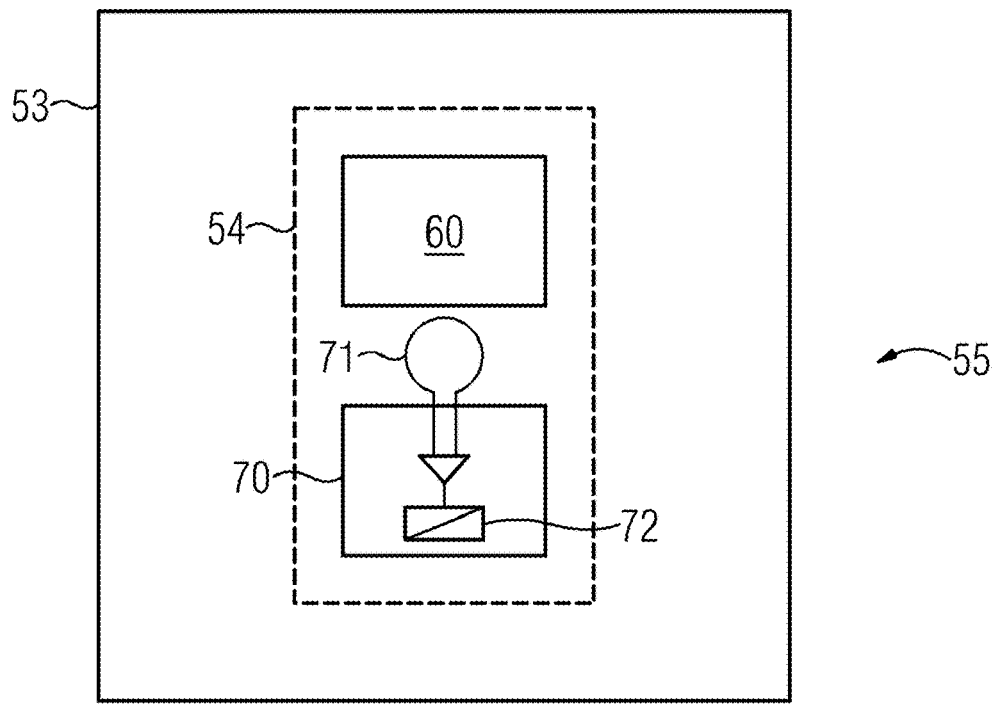
FIG. 3 depicts a diagrammatic view of an example of electronic apparatus.

FIG. 3 shows a diagrammatic view of an exemplary electronic apparatus in detail. The view here is generic, the sources of interference 61, 62, 63, 64, 65 of FIG. 2 are represented here by the source of interference 60, the different electronic apparatuses 50, 51, 52 and further electronic apparatuses extending beyond them by the generic electronic apparatus 55.

In FIG. 3, the sensor 70 detects an interfering high-frequency alternating magnetic field by an antenna loop 71 through induction, amplifies, and digitizes the interfering HF alternating magnetic field by an A/D converter in order to transmit it to the control unit 20 of the magnetic resonance tomography unit for interference suppression. It is also conceivable to detect an interfering high-frequency alternating electrical field by an electrical antenna such as a dipole or monopole. The electrical and magnetic components of the high-frequency alternating field are linked to one another via the Maxwell field equations, so that the antennae shown also each provide information for the other component.

In one embodiment, the electronic apparatus 55 includes a shield 54 that completely or partially encloses the source of interference 60 and the sensor 70. In this way, a high-frequency power output of the source of interference 60 emitted into the space surrounding the electrical apparatus 55 is reduced. Conversely, a magnetic resonance signal detected by the sensor 70 is thereby reduced or minimized. If this magnetic resonance component is treated as an interference signal in subsequent interference suppression or image reconstruction, this leads to additional artifacts in the acquired images. As a result of the shield 54, these additional artifacts may thus be reduced and/or the interference suppression may be improved or simplified by the separation of the signals.

Because the shield 54, as in FIG. 3, surrounds only the source of interference 60 and the sensor 70, the shield 54 may be kept small in dimensions, so that effects on the magnetic fields of the field magnet 11 and the gradient coils 12 as well as the high-frequency electromagnetic alternating fields for exciting the nuclear spin may be kept small. Furthermore, by selecting suitable materials, or metals, for example, not magnetic or ferromagnetic metals or metals with low magnetic susceptibility or geometry, for example, with slots to avoid eddy currents, a disadvantageous effect on field homogeneity may be kept to a minimum. This is particularly important in the case of a local coil 50 as an electronic apparatus because this is arranged directly on the region to be captured during image acquisition.

Figure 4:
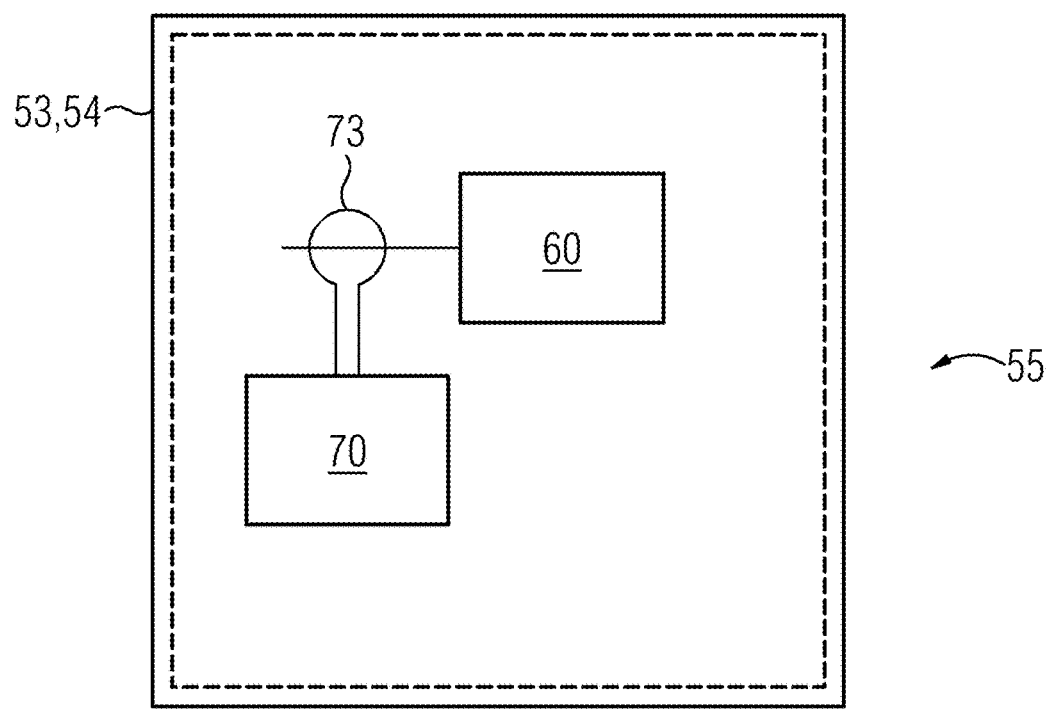
FIG. 4 depicts a diagrammatic view of an example of electronic apparatus.

FIG. 4 shows a further embodiment of an electronic apparatus. For one thing, this differs in that interference fields of the source of interference are not detected by an alternating field emitted into the room, but rather the interference field is detected by the causative currents or voltages. By way of example, an induction loop 73 is shown here around a current-carrying conductor. However, capacitive coupling for detecting voltages or the use of directional couplers for detecting high-frequency signals propagating on the line, in particular, also the propagation direction thereof, are also conceivable. The directional couplers may also be used to distinguish between interference emitted from or introduced into the source of interference.

Furthermore, the embodiment of FIG. 4 differs in that the shield 54 surrounds not only the source of interference 60 and the sensor 70, but the entire electronic apparatus 55. It is conceivable that the shield 54 thereby also simultaneously forms a housing for the electronic apparatus.

It is also possible that no separate sensor 70 is present as a detector of a source of interference or its generated electromagnetic interference fields, but the detector is part of the electronic apparatus. For example, the electronic apparatus may have a controller that itself is the source of interference or controls the source of interference. The controller may then send information as a detector, for example, about the time and the type of activity, to the magnetic resonance tomography unit 1 or its controller 23. The detector may also be implemented as a program element on the controller of the electronic apparatus and, for example, send information about the type and time of active subroutines as information.

Furthermore, different combinations of the features shown in FIG. 3 and FIG. 4 are also conceivable in the context of the electronic apparatus.

Figure 5:
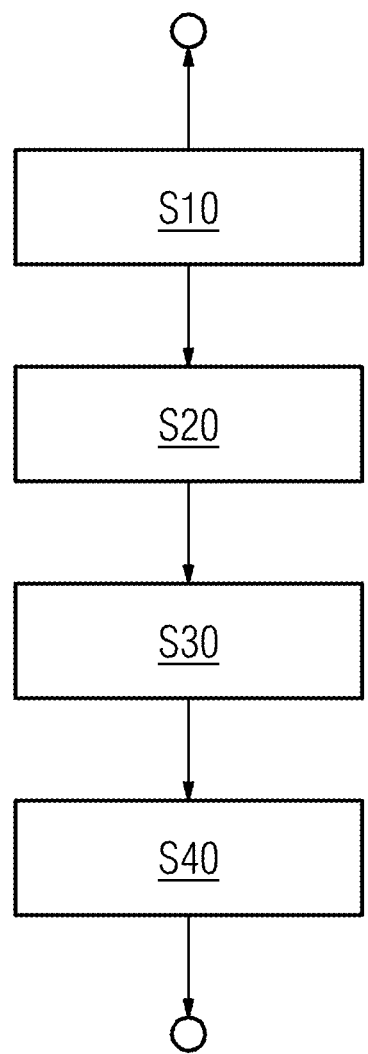
FIG. 5 depicts a diagrammatic view of a flow chart of an embodiment of the method.

FIG. 5 shows a diagrammatic view of a flow chart of an embodiment of the method. The method is carried out on a system with an electronic apparatus, as described with reference to the preceding figures.

In act S20, the high-frequency unit 21 emits an excitation pulse for nuclear spins of an object under examination via the body coil 14 or a local coil 50 under the control of the controller 23.

In act S30, the high-frequency unit 21 receives a magnetic resonance signal of the object under examination by the magnetic resonance tomography unit 1 via the body coil 14, or, e.g., via the local coil 50 as a receiving antenna. The received magnetic resonance signal may also have interference components that are emitted by a source of interference 60 of the electronic apparatus 55.

In order to reduce the interference signal in the received magnetic resonance signal and/or to reduce disadvantageous effects caused by the interference signal in a subsequent image reconstruction, knowledge of or information about the interference signal is required.

In act S40, the magnetic resonance tomography unit 1 therefore receives information from the detector 70 about the source of interference 60.

The information may be a signal with an analog or digital representation of the electrical and/or magnetic field strength of the interference signal, as detected by the sensor 70. This may be obtained, for example, by receiving the electromagnetic interference field with a receiving antenna from the sensor 70. The signal may subsequently be processed, (e.g., amplified, filtered, converted, and/or digitized) in frequency and transmitted from the sensor 70 to the high-frequency unit 21 in order to be used there in further signal processing for the reduction of interference, as described below with respect to act S50. The temporal relation or phase relationship to the received magnetic resonance signal may be obtained or additionally stored.

It is also conceivable that information about the interference signal is already extracted. For example, the time of the interference signal may be transmitted in order to subsequently identify and newly acquire or interpolate the data affected by interference. It is also conceivable that frequency information and or phase information is acquired and transmitted so that faulty data in the k-space may be recognized and corrected during the image reconstruction.

In act S50, the effect of the interference signal or the electromagnetic interference field of the source of interference during image acquisition is subsequently reduced with the aid of the signal to the detected electromagnetic interference fields.

It is conceivable, for example, for a phase relationship and an amplitude relationship to be determined between a portion of the interference signal in the received magnetic resonance signal. This may be determined, for example, by autocorrelation of the received magnetic resonance signal and the signal of the sensor 70. Calibration is also conceivable, e.g., by receiving an "empty" magnetic resonance signal without previously exciting the signal, so that only the portion of the interference signal remains. On the basis of the determined phase relationship and amplitude ratios, the signal of the sensor 70 may thus be attenuated and delayed accordingly so that, upon addition of the received magnetic resonance signal and the adapted sensor signal, a destructive interference occurs, which reduces a portion of the sensor signal in the magnetic resonance signal. For example, an optimization method for delay and attenuation is also conceivable, in which the energy of the sum signal is minimized. Simpler methods are also conceivable, (e.g., an adaptive filter that suppresses the frequencies of the interference signal), but which are subsequently taken into account in image reconstruction in order to avoid artifacts. Methods of machine learning and artificial intelligence may also be used to predict a resulting disturbance in the MR signal from the sensor signal and to reduce it, for example, by destructive interference.

In principle, it is also conceivable for the information about the interference signal to be taken into account in act S50 only during the image reconstruction. For example, the position of disturbed measurement points in the k-space may be identified via the time and/or frequency and phase position of the interference signal. The disturbed measurement points may then be interpolated or newly acquired, for example.

The combination of both options, (i.e., suppression in the received magnetic resonance signal and additional corrections during image reconstruction), is also possible.

In particular, if a reduction of the interference signal does not take place in real time, it is conceivable that the detector does not detect the interference signal itself, but only transmits a time and information about the source of interference, for example, about the activity performed by the source of interference at that time.

In one embodiment of the method, in act S10, reference data about the activity may be acquired. For example, samples of the electromagnetic interference fields generated by the source of interference during the activity, or spectral information characteristic thereof, are conceivable. The reference data is stored. In act S50, for example, the information from the detector may be used to identify a time window in the magnetic resonance data that may be disturbed by the activity. By an autocorrelation of reference data and magnetic resonance data, the interference signal may then be identified by the activity in this time window and reduced or eliminated, for example, by subtraction. If the interference caused by the activity is not identical, a reduction may nevertheless take place on the basis of characteristic properties, for example, by filtering frequency bands of the interference signal. Use of the reference data acquired in act S10 to train an aforementioned neural network is also conceivable.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. An electronic apparatus for a magnetic resonance tomography unit, the electronic apparatus comprising:
   a detector comprising a sensor configured to detect a source of interference comprising electromagnetic interference fields generated by the electronic apparatus itself; and
   a signal output configured to transmit information about the electromagnetic interference fields to the magnetic resonance tomography unit,
   wherein the electronic apparatus is a local coil and the source of interference is an analog-to-digital converter of the local coil and/or a transmitting antenna of the local coil; or
   wherein the electronic apparatus is a tablet computer configured to operate the magnetic resonance tomography unit and the source of interference is a processor of the tablet computer and/or a display of the tablet computer; or
   wherein the electronic apparatus is a camera configured to monitor a patient during operation of the magnetic resonance tomography unit.

2. The electronic apparatus of claim 1, wherein the sensor is arranged in an immediate vicinity of the source of interference.

3. The electronic apparatus of claim 2, wherein the electronic apparatus comprises a shield, and
   wherein the sensor and the source of interference of the electromagnetic interference fields are entirely enclosed by the shield.

4. The electronic apparatus of claim 1, wherein the electronic apparatus comprises a shield, and
   wherein the sensor and the source of interference of the electromagnetic interference fields are entirely enclosed by the shield.

5. The electronic apparatus of claim 1, wherein the electronic apparatus is the local coil of the magnetic resonance tomography unit.

6. A magnetic resonance tomography unit comprising:
a local coil comprising: a detector comprising a sensor configured to detect a source of interference comprising electromagnetic interference fields generated by the local coil itself; and a signal output configured to transmit information about the electromagnetic interference fields to the magnetic resonance tomography unit; and
a signal input configured to be in signal connection with the signal output of the local coil,
wherein the signal input is configured to receive the information about the source of interference from the local coil and perform an image acquisition as a function of the information.

7. The magnetic resonance tomography unit of claim 6, wherein the sensor is arranged in an immediate vicinity of the source of interference of the electromagnetic interference fields.

8. The magnetic resonance tomography unit of claim 7, wherein the local coil comprises a shield, and
wherein the sensor and the source of interference of the electromagnetic interference fields are entirely enclosed by the shield.

9. The magnetic resonance tomography unit of claim 6, wherein the local coil comprises a shield, and
wherein the sensor and the source of interference of the electromagnetic interference fields are entirely enclosed by the shield.

10. The magnetic resonance tomography unit of claim 6, wherein the magnetic resonance tomography unit is further configured to emit an excitation pulse via the local coil for nuclear spins of an object under examination.

11. The magnetic resonance tomography unit of claim 6, wherein the source of interference is an analog-to-digital converter of the local coil and/or an antenna of the local coil.

12. A method for operating a system, the method comprising:
emitting an excitation pulse for nuclear spins of an object under examination by a magnetic resonance tomography unit;
receiving a magnetic resonance signal of the object under examination by a receiving antenna of the magnetic resonance tomography unit;
receiving information about a source of interference by an electronic apparatus of the magnetic resonance tomography unit, wherein the electronic apparatus comprises a sensor that detects electromagnetic interference fields generated by the electronic apparatus itself; and
reducing an effect of the source of interference during an image acquisition as a function of the information about the source of interference,
wherein the electronic apparatus is a local coil and the source of interference is an analog-to-digital converter of the local coil and/or a transmitting antenna of the local coil; or
wherein the electronic apparatus is a tablet computer operating the magnetic resonance tomography unit and the source of interference is a processor of the tablet computer and/or a display of the tablet computer; or
wherein the electronic apparatus is a camera monitoring a patient during operation of the magnetic resonance tomography unit.

13. The method of claim 12, further comprising:
transmitting, by the electronic apparatus, the information about the electromagnetic interference fields to the magnetic resonance tomography unit by a signal output of the electronic apparatus.

14. The method of claim 12, wherein, in the reducing, suppression control of the magnetic resonance tomography unit reduces a proportion of the magnetic resonance signal generated by electromagnetic interference fields of the source of interference.

15. The method of claim 12, wherein, in the reducing, in an image reconstruction by the magnetic resonance tomography unit, image artifacts caused by the source of interference are reduced.

16. The method of claim 12, further comprising:
acquiring reference data relating to the source of interference; and
reducing the effect of the source of interference in the image acquisition as a function of the reference data.

17. The method of claim 12, wherein the emitting of the excitation pulse is conducted via the electronic apparatus.

18. The method of claim 17, wherein the electronic apparatus is the local coil.

* * * * *